United States Patent [19]
Jempolsky

[11] Patent Number: 5,843,125
[45] Date of Patent: *Dec. 1, 1998

[54] SKIN CONTRACTOR

[76] Inventor: Lawrence Jempolsky, 2125 Bath Ave., Brooklyn, N.Y. 11214

[ * ] Notice: The terminal 11 months of this patent has been disclaimed.

[21] Appl. No.: 478,350

[22] Filed: Jun. 7, 1995

[51] Int. Cl.$^6$ .................................................. A61B 17/00
[52] U.S. Cl. .................... 606/218; 606/213; 606/215; 606/207
[58] Field of Search .................... 606/212–213, 606/215–218, 139, 148, 151, 205, 207–208, 210–211; 81/3.56, 3.48, 318, 328, 336–338, 418, 426, 426.5, 424.5

[56] References Cited

U.S. PATENT DOCUMENTS

| | | | |
|---|---|---|---|
| 1,756,670 | 4/1930 | Treat | 606/151 |
| 3,470,872 | 10/1969 | Grieshaber | 606/207 |
| 3,489,151 | 1/1970 | Eller | 606/210 |
| 4,506,669 | 3/1985 | Blake, III | 606/218 |
| 4,955,897 | 9/1990 | Ship | 606/210 |
| 5,176,702 | 1/1993 | Bales et al. | 606/208 |
| 5,251,642 | 10/1993 | Handlos | 606/148 |
| 5,383,898 | 1/1995 | Sarfarazi | 606/215 |
| 5,425,740 | 6/1995 | Hutchinson, Jr. | 606/215 |

Primary Examiner—Jeffrey A. Schmidt
Attorney, Agent, or Firm—Patrick J. Walsh

[57] ABSTRACT

A surgical instrument for gripping and applying tension to and closing separated skin edges as needed to suture a wound.

4 Claims, 2 Drawing Sheets

SKIN CONTRACTOR

BACKGROUND OF THE INVENTION

The present invention relates to surgical instruments, and particularly to those used for veterinary surgical procedures.

In performing surgery, it is sometimes necessary to remove extensive areas of skin as, for example, in the case of tumor excision. When closing the wound, it is necessary to apply tension to draw the edges of skin into proper apposition for suturing.

The present invention provides an instrument for applying tension to skin in such cases.

SUMMARY OF THE INVENTION

The present invention comprises a handheld instrument for applying tension to separated skin edges when needed to suture a wound.

In a preferred embodiment of the invention, a skin contractor comprises a handheld and manipulated instrument with general appearance of the letter A. The instrument includes elongated arms joined along a pivot axis at their top ends, and with finger loops formed at the lower end of each arm. A rachet and pawl mechanism interconnects each of the arms so that the arms are held in fixed position with respect to each other. The upper portion of the arms have inner, confronting surfaces lined with inwardly projecting pins for engaging spaced edges of skin on opposite sides of a wound. The instrument, in open position, engages the spaced edges of skin along the confronting pins. By closing the instrument, the skin edges are tensioned and drawn together for suturing. The ratchet and pawl mechanism holds the instrument arms and skin edges in fixed position with respect to each other so that the surgeon can unhand the instrument and perform the necessary suturing.

OBJECTS OF THE INVENTION

It is an object of the invention to provide a surgical instrument for tensioning skin in the vicinity of a wound.

It is an object of the invention to provide a handheld and manipulated instrument for engaging a substantial length of skin on both sides of a wound for drawing the skin edges together for suturing.

It is a further object of the invention to provide a skin contractor with pivoted arms and skin piercing pins for enabling a surgeon to draw the skin over a wound for suturing.

It is a further object of the invention to provide skin contractor which draws skin over a wound and holds the skin in fixed position thereby enabling a surgeon to unhand the instrument and continue with the surgical procedure.

It is a further object of the invention to provide a skin contactor fitted with a set of confronting pins enabling a surgeon to draw skin over a wound with minimum harm to the skin in the vicinity of the wound.

Other and further objects of the invention will occur to one skilled in the art with an understanding of the following detailed description of the invention or upon employment of the invention in practice.

DESCRIPTION OF THE DRAWING

A preferred embodiment of the invention has been chosen for purposes of illustrating the construction and operation of the invention and is shown in the accompanying drawing in which.

DETAILED DESCRIPTION OF THE INVENTION

Figure 2:
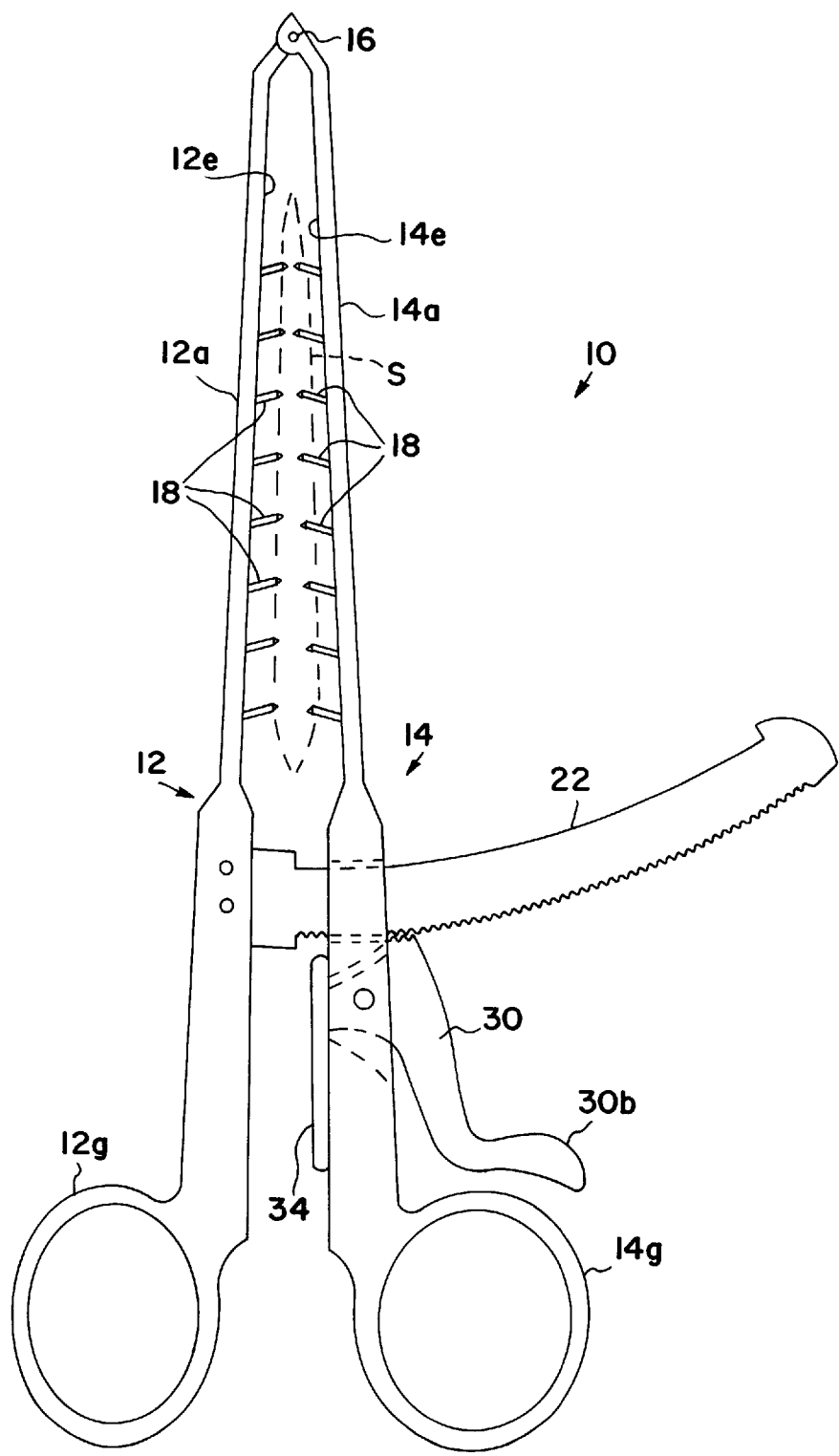
FIG. 2 is a side elevational view of an instrument of the invention, illustrating the instrument in closed position.

Referring now to the drawing, a preferred embodiment of skin contractor according to the invention comprises an instrument 10 having elongate arms 12, 14 of similar construction with a thin upper portions 12a, 14a and heavier lower portions 12b, 14b. The arms are joined at their top ends 12c, 14c by a rivet 16 or similar fastener defining a pivot axis. Short lengths 12d, 14d of the terminal portions of the elongate arms are directed at an angle toward each other for the purpose of spacing the inner surfaces 12e, 14e of the elongate arms thereby allowing them to be aligned nearly parallel to each other when the instrument is in closed position as shown in FIG. 2. The spacing of the inner surfaces of the upper portions of the arms is also facilitated by the presence of shoulders 12f, 14f at the junction of upper and lower arm portions.

Each arm has a finger loop 12g, 14g formed integral at its lower end for holding the instrument and manipulating the pivoted arms with thumb and forefinger.

The upper portions of the arms have inner, confronting surfaces 12e, 14e lined with inwardly projecting sharp pins 18 for piercing and engaging spaced edges of skin on opposite sides of a wound. As illustrated in the drawing, the pins are aligned in point-to-point relationship for holding skin edges in place while being sutured. If desired the pins may be offset with the pins of one arm coming to rest in the space between adjacent pins of the other arm when the instrument is closed.

Figure 1:
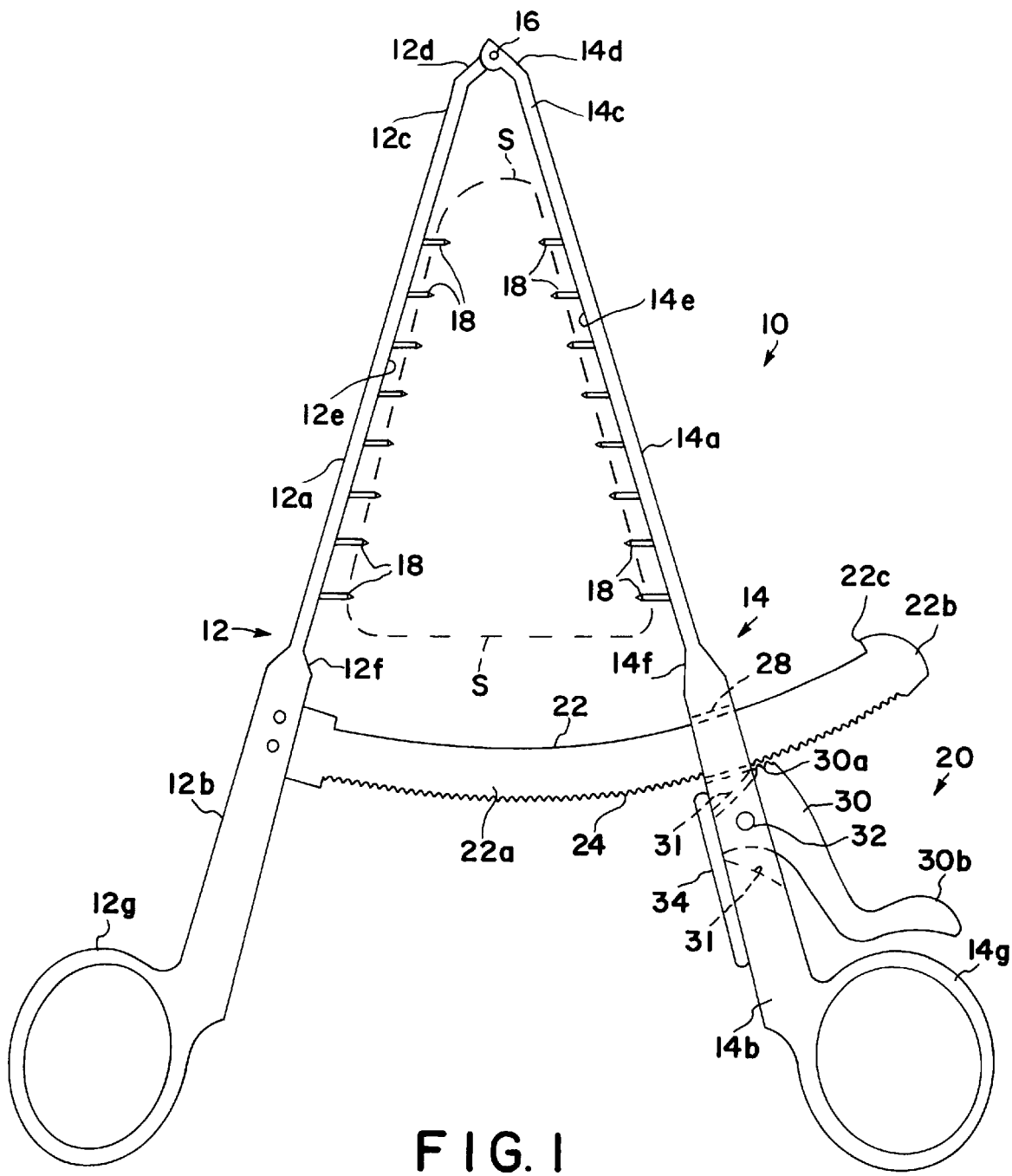
FIG. 1 is a side elevational view of an instrument of the invention, illustrating the instrument in open position.

A ratchet and pawl mechanism 20 interconnects each of the arms so that the arms may be held in fixed position with respect to each other. A ratchet arm 22 in the form of an arc of a circle of radius r is affixed to one instrument arm (preferably the arm fitted with the thumb loop 12g) is provided with ratchet teeth 24 along its lower surface 22a, and extends through a slot 28 in the lower portion of the other arm 14. The outer end 22b of the ratchet arm terminates in a retaining ledge 22c for limiting outward pivotal movement of one instrument arm with respect to the other. A pawl 30 having a section of ratchet teeth 30a is pivotally attached to a slot 31 in arm 14 by a rivet 32. Preferably, the pawl cooperates with a leaf spring 34 affixed to arm 14 for biasing the pawl in a counterclockwise direction (FIG. 1) for normal engagement with the ratchet arm. The pawl has an actuating handle 30b positioned adjacent the finger loop 14g for ease of finger manipulation for disengaging the pawl mechanism.

The instrument, in open position (FIG. 1), engages the spaced edges of skin S by means of the confronting pins. By closing the instrument (FIG. 2), the skin edges are tensioned and drawn together for suturing. The ratchet and pawl mechanism holds the instrument arms in fixed position with respect to each other so that the surgeon can unhand the instrument and perform the necessary suturing while the instrument arms hold the skin edges securely in proper apposition.

I claim:

1. A skin contractor comprising a pair of elongated arms having top and bottom ends with the arms joined along a pivot axis at their top ends, the arms further having finger loops at their bottom ends, each arm having an upper portion with inner, confronting surfaces, means lining each of the inner, confronting surfaces for engaging spaced edges of skin on opposite sides of a wound so that by closing the instrument the skin edges are tensioned and drawn together for suturing, the lining means being confined to the upper portion of the arms with the lower portion devoid of such lining means, the lower portion of each arm being joined to the upper portion of each arm and extending therefrom terminating at the said finger loops, means positioned below the upper portion of the arms for interconnecting the arms so that the arms may be held in fixed position with respect to each other whereby a surgeon can unhand the instrument and perform the suturing.

2. A skin contractor comprising a pair of elongated arms joined along a pivot axis at their top ends, and having finger loops formed at the lower end of each arm, each arm having an upper portion and a lower portion the upper portion, of the arms having inner, confronting surfaces, a plurality of inwardly projecting pins lining each of the inner, confronting surfaces of the upper arm portions for engaging spaced edges of skin on opposite sides of a wound so that by dosing the instrument the skin edges are tensioned and drawn together for suturing, the inwardly projecting pins being confined to the upper portion of the arms with the lower portion devoid of pins, the lower portion of each arm being joined to the upper portion of each arm and extending therefrom terminating at the said finger loops, a ratchet and pawl mechanism interconnecting the arms so that the arms may be held in fixed position with respect to each other whereby a surgeon can unhand the instrument and perform the suturing, and the rachet and pawl mechanism positioned below the upper portion of the arms.

3. A skin contractor comprising a pair of elongate arms joined along a pivot axis at their top ends with each elongate arm divided into upper and lower arm portions of approximately the same length, the top terminal portion of each arm being directly inwardly at an angle to permit approximate parallel alignment of the arms, each arm having a finger loop formed at its lower end, each arm having an upper portion with inner, confronting surfaces, a plurality of sharp pins lining each of the inner, confronting surfaces of the upper portion of each arm for engaging spaced edges of skin on opposite sides of a wound so that by moving the arms into parallel relationship the skin edges are tensioned and drawn together for suturing, the inwardly projecting pins being confined to the upper portion of the arms with the lower portion devoid of pins, a ratchet arm affixed to one elongate arm and passing through a slot in the other elongate arm, a pawl pivotally mounted on the other elongate arm for engagement with the ratchet arm for holding the elongate arms in fixed position with respect to each other whereby a surgeon can unhand the instrument and perform the suturing, means for biasing the pawl into engagement with the ratchet arm, and the ratchet and pawl mechanism being positioned below the upper portion of the arms.

4. A skin contractor as defined in claim 3 in which the pawl has an actuating handle positioned adjacent the finger loop of said other elongate arm for disengaging the pawl mechanism.

\* \* \* \* \*